(12) United States Patent
Csoma et al.

(10) Patent No.: US 9,286,442 B2
(45) Date of Patent: Mar. 15, 2016

(54) TELECARE AND/OR TELEHEALTH COMMUNICATION METHOD AND SYSTEM

(71) Applicant: General Electric Company, Schenectady, NY (US)

(72) Inventors: Csenge Csoma, Budapest (HU); Akos Erdos, Budapest (HU); Alan Davies, Berks (GB)

(73) Assignee: General Electric Company, Schenectady, NY (US)

(*) Notice: Subject to any disclaimer, the term of this patent is extended or adjusted under 35 U.S.C. 154(b) by 699 days.

(21) Appl. No.: 13/631,237

(22) Filed: Sep. 28, 2012

(65) Prior Publication Data
US 2013/0085758 A1   Apr. 4, 2013

(30) Foreign Application Priority Data
Sep. 30, 2011 (EP) .................................. 11462015

(51) Int. Cl.
G06F 19/00 (2011.01)
(52) U.S. Cl.
CPC .......... *G06F 19/345* (2013.01); *G06F 19/3418* (2013.01)
(58) Field of Classification Search
CPC ................................................ G06F 17/30032
See application file for complete search history.

(56) References Cited

U.S. PATENT DOCUMENTS

| | | | |
|---|---|---|---|
| 5,339,821 A | 8/1994 | Fujimoto | |
| 5,390,238 A * | 2/1995 | Kirk et al. | 379/106.02 |
| 5,573,506 A | 11/1996 | Vasko | |
| 5,646,912 A | 7/1997 | Cousin | |
| 5,917,414 A | 6/1999 | Oppelt et al. | |
| 5,966,691 A * | 10/1999 | Kibre et al. | 704/260 |
| 6,418,440 B1 * | 7/2002 | Kuo et al. | |
| 6,510,962 B1 | 1/2003 | Lim | |
| 6,537,214 B1 | 3/2003 | Hood et al. | |
| 6,607,484 B2 * | 8/2003 | Suzuki et al. | 600/300 |
| 6,721,706 B1 * | 4/2004 | Strubbe et al. | 704/275 |
| 6,731,307 B1 * | 5/2004 | Strubbe et al. | 715/727 |
| 6,757,362 B1 * | 6/2004 | Cooper et al. | 379/88.01 |
| 6,795,808 B1 * | 9/2004 | Strubbe et al. | 704/275 |
| 6,908,431 B2 * | 6/2005 | Bardy | 600/300 |

(Continued)

OTHER PUBLICATIONS

Su, Chuan-Jun, and Chia-Ying Wu. "JADE implemented mobile multi-agent based, distributed information platform for pervasive health care monitoring." Applied Soft Computing 11.1 (2011): 315-325.*

(Continued)

*Primary Examiner* — Matthew Baker
(74) *Attorney, Agent, or Firm* — GE Global Patent Operation; Marc A. Vivenzio

(57) ABSTRACT

A telecare and/or telehealth communication method is described. The method comprises providing predetermined voice messages configured to ask questions to or to give instructions to an assisted individual, providing an algorithm configured to communicate with the assisted individual, and communicating at least one of the predetermined voice messages configured to ask questions to or to give instructions to the assisted individual. The method further comprises analyzing a responsiveness and/or compliance characteristics of the assisted individual, and providing the assisted individual with voice messages in a form most acceptable and effective for the assisted individual on the basis of the analyzed responsiveness and/or the analyzed compliance characteristics.

37 Claims, 6 Drawing Sheets

(56) References Cited

U.S. PATENT DOCUMENTS

| | | | |
|---|---|---|---|
| 6,990,179 B2* | 1/2006 | Merrow et al. ................ 379/69 |
| 7,024,367 B2 | 4/2006 | Amano et al. |
| 7,447,643 B1* | 11/2008 | Olson et al. ........................ 705/2 |
| 7,547,278 B2* | 6/2009 | Miyazaki et al. ............. 600/300 |
| 7,587,469 B2* | 9/2009 | Brown ........................ 709/217 |
| 7,624,028 B1* | 11/2009 | Brown .............................. 705/3 |
| 7,656,299 B2 | 2/2010 | Gentry et al. |
| 7,840,420 B2* | 11/2010 | Brown ............................... 705/2 |
| 7,925,508 B1* | 4/2011 | Michaelis ..................... 704/270 |
| 7,957,837 B2* | 6/2011 | Ziegler et al. ................. 700/258 |
| 7,979,284 B2* | 7/2011 | Brown ............................... 705/2 |
| 8,010,358 B2* | 8/2011 | Chen ............................ 704/246 |
| 8,170,609 B2* | 5/2012 | Hedtke et al. ............. 455/556.1 |
| 8,209,051 B2* | 6/2012 | Wang et al. ................... 700/245 |
| 8,442,835 B2* | 5/2013 | Ji et al. ........................... 704/272 |
| 8,594,839 B2* | 11/2013 | Hanson ........................ 700/245 |
| 8,706,523 B2* | 4/2014 | Kulawiec et al. ................. 705/2 |
| 8,712,790 B1* | 4/2014 | Brown ............................... 705/2 |
| 8,838,513 B2* | 9/2014 | Sudharsan ..................... 706/25 |
| 8,990,336 B2* | 3/2015 | Brown ........................ 709/217 |
| 2002/0035486 A1* | 3/2002 | Huyn et al. ....................... 705/3 |
| 2003/0069752 A1* | 4/2003 | LeDain et al. .................... 705/2 |
| 2004/0015132 A1* | 1/2004 | Brown ........................ 604/131 |
| 2005/0144002 A1 | 6/2005 | Ps |
| 2006/0154642 A1 | 7/2006 | Scannell, Jr. |
| 2006/0173267 A1 | 8/2006 | Chiang |
| 2007/0192910 A1* | 8/2007 | Vu et al. .......................... 901/17 |
| 2008/0096533 A1* | 4/2008 | Manfredi et al. .......... 455/412.1 |
| 2008/0102056 A1* | 5/2008 | Bradford ............ G06Q 30/0217 424/85.5 |
| 2009/0044112 A1* | 2/2009 | Basso et al. ................... 715/706 |
| 2010/0026817 A1* | 2/2010 | Ryan et al. ................ 348/207.11 |
| 2011/0016064 A1* | 1/2011 | Barton ............................ 706/11 |
| 2011/0123971 A1* | 5/2011 | Berkowitz et al. ............. 434/308 |
| 2011/0288878 A1* | 11/2011 | Blair ................................. 705/2 |
| 2012/0077167 A1* | 3/2012 | Weideman ..................... 434/262 |
| 2012/0083669 A1* | 4/2012 | Abujbara ...................... 600/300 |
| 2012/0116186 A1* | 5/2012 | Shrivastav ........... A61B 5/0507 600/301 |
| 2012/0246102 A1* | 9/2012 | Sudharsan ..................... 706/25 |

OTHER PUBLICATIONS

Boger, Jennifer, et al. "A planning system based on Markov decision processes to guide people with dementia through activities of daily living." Information Technology in Biomedicine, IEEE Transactions on 10.2 (2006): 323-333.*

Corchado, Juan M., et al. "Intelligent environment for monitoring Alzheimer patients, agent technology for health care." Decision Support Systems 44.2 (2008): 382-396.*

Looije, Rosemarijn, Fokie Cnossen, and Mark A. Neerincx. "Incorporating guidelines for health assistance into a socially intelligent robot." Robot and Human Interactive Communication, 2006. ROMAN 2006. The 15th IEEE International Symposium on. IEEE, 2006.*

Kessens, Judith M., et al. "Facial and vocal emotion expression of a personal computer assistant to engage, educate and motivate children." Affective Computing and Intelligent Interaction and Workshops, 2009. ACII 2009. 3rd International Conference on. IEEE, 2009.*

D.L. Roter, Studies of doctor-patient interaction, Annual Reviews Public Health, (1989) 10: 163-80.

* cited by examiner

TELECARE AND/OR TELEHEALTH COMMUNICATION METHOD AND SYSTEM

CROSS-REFERENCE TO RELATED APPLICATIONS

This application claims foreign priority benefits under 35 U.S.C. §119 to co-pending European Patent Application Serial No. 11462015.6, filed Sep. 30, 2011, which is hereby incorporated by reference in its entirety as part of the present disclosure.

BACKGROUND OF THE INVENTION

Embodiments of the present invention relate generally to remote health monitoring and, more particularly, to a telecare and/or telehealth communication method and a system for providing remote health monitoring.

Health monitoring of elderly individuals or patients released from hospital in their homes is getting more and more important as hospitals are often overcrowded, too far or too expensive on a long term basis. Many attempts have been made in the past in order to facilitate remote health care of elderly people, and to suggest methods and systems for providing health monitoring data for care givers at different levels from medical specialists, through health care personnel to family members. The ultimate goal would be to ease the burden of the health- and social-care systems as well as improve quality of life of such individuals needing assistance in their homes.

These individuals are usually elder people, usually having a chronic condition, sometimes neurological diseases, who have difficulties using new technologies and are usually suffering from perceived loneliness. They usually have a long term medication, and simultaneously health-related data have to be collected, stored and evaluated in order to provide the required telecare and telehealth services. The measurements, required by the health-related data acquisition, are in most of the cases performed by the patients, without any supervision.

It is extremely important to get and maintain motivation in repeating activities, especially when the repeating activities are useful but unpleasant or boring. It is also extremely challenging to get the elder population and those with chronic neurological diseases interested in and committed to new technologies used in telecare and telehealth. Sometimes initially, the user is interested in the new technologies but becomes bored due to the predictability of the communication with the telecare/telehealth devices.

From psychological point of view, the most effective solution to familiarize the elderly with the new systems is the personalization of the parts and services of the system which are used as communication interface, e.g. the communicator center of the system (also called home hub or health monitoring control unit or subsystem control unit). There are plenty of available technologies for personalization of a computational device, and the amount of applicable innovation is growing: for example videoconferencing or reminder messages are already used in some telemedicine systems, however these technologies rely on human-to-human communication. A telemedicine system consisting of a remote center configured to examine a patient, communicating with a diagnostic center, and enabling a doctor to provide medical care via video conference is described in U.S. patent application Ser. No. 11/022,566 (Method and device for administering health care remotely, to Chun Hsien Chiang et al.). U.S. patent application Ser. No. 10/228,034 (Method and device for administering health care remotely, to Chun Hsien Chiang et al.) describes a remote health-monitoring system and method for the remote monitoring and supervision of outpatient vital signs using videoconferencing techniques.

Other developments focus on solutions based on man-machine communication. U.S. Pat. No. 5,339,821 suggests for example a home medical system and medical apparatus for use therewith, which gives a patient instructions via display and sound messages. This sound is only indicative for the presence of a new message to be read by the patient. U.S. Pat. No. 6,510,962 describes a programmable automatic pill dispenser, which already uses human voice messages to give instructions to a patient. U.S. Pat. No. 6,537,214 suggests to use messages in the native language and dialect spoken, where the monitoring takes place. U.S. Pat. No. 5,917,414 suggests to select the voice of a relative or a friend. U.S. Pat. No. 5,390,238 proposes a health support system that uses two-way communication between the patient and the care providing system and finally U.S. Pat. No. 5,646,912 describes a medication compliance, coordination and dispensing system which has I/O devices for visual and audible alarms for alerting the patient of administration times, voice and display means for providing extended medication information to the patient and a mini camera for recording patient compliance.

Most of the prior art methods and systems provide only limited communication possibilities which are far from conventional human-human communication. Nor the voice or the video communication can be as effective as the human-to-human communication, which however is in most cases not applicable because of the above mentioned reasons.

Research has shown the importance of non-verbal communication in patient-doctor interaction as described in "Studies of doctor-patient interaction", Annual Reviews Public Health, (1989) 10: 163-80 by D. L. Roter and J. A. Hall. The tonal or other features of vocal communication have been assessed: correlation has been found between doctors' voice quality and their success in referring the patients to treatment. It has been also demonstrated that the particular vocal affects expressed when talking about patients are reflected in clinicians' talk to the same patients, and also that a physician's voice tone relates various patient effects. In another study physicians' abilities to express emotions through the face and voice and to decode the meanings of nonverbal cues of the face and voice have been shown to be related to both patient satisfaction and appointment keeping compliance. Although it is not yet known exactly how these nonverbal skills are put to use in the medical visit, it is clear that they play an important role.

Research has also shown that people vary in their ability to send and receive non-verbal communication signs so it is important to have a personalized system when using non-verbal communication signs.

Due to the imperfection of the prior art methods and systems, there is a continuous need for providing a machine-to-human communication which comes as near as possible to the human-to-human communication and which is less expensive than human-to-human communication and more acceptable than the prior and present man-machine communication systems.

BRIEF SUMMARY OF THE INVENTION

According to an embodiment of the present invention, there is provided a telecare and/or telehealth communication method. The method comprises providing predetermined voice messages configured to ask questions to or to give instructions to an assisted individual; providing an algorithm configured to communicate with the assisted individual; and communicating at least one of the predetermined voice messages configured to ask questions to or to give instructions to the assisted individual. The method further comprises analyzing a responsiveness and/or compliance characteristics of the assisted individual; and providing the assisted individual with voice messages in a form most acceptable and effective for the assisted individual on the basis of the analyzed responsiveness and/or the analyzed compliance characteristics.

According to an embodiment of the present invention, there is provided a telecare and/or telehealth communication system. The system comprising a plurality of subsystems at the location of an assisted individual, wherein the plurality of subsystems comprises a subsystem control unit and at least one information collecting unit configured to collect information from and relating to the assisted individual, wherein at least one of the at least one information collecting unit is configured to communicate with the subsystem control unit; a central data server station configured to communicate with the plurality of subsystems; and monitoring side terminals configured to communicate with the central data server station and to provide information to health care professionals, care giving personnel, and/or authorized family members. Furthermore, the subsystem control unit comprises a communication storage configured to store a series of predetermined voice messages configured to ask questions to or to give instructions to the assisted individual; a program configured to determine an algorithm configured to communicate with the assisted individual, an output communication configured to communicate voice messages in order to ask questions to or to give instructions to an assisted individual, at least one information collecting unit; a first processor configured to analyze and to evaluate information collected by the at least one information collecting unit with respect to a responsiveness and/or compliance characteristics of the assisted individual; and a second processor configured to determine the voice messages in a form most acceptable and effective for the assisted individual on the basis of the analyzed responsiveness and/or the analyzed compliance characteristics.

BRIEF DESCRIPTION OF THE DRAWINGS

These and other features, aspects and advantage of the embodiments of the present invention can be better understood when the following detailed description are read with reference to the accompanying drawings, in which.

DETAILED DESCRIPTION OF THE INVENTION

Figure 1:
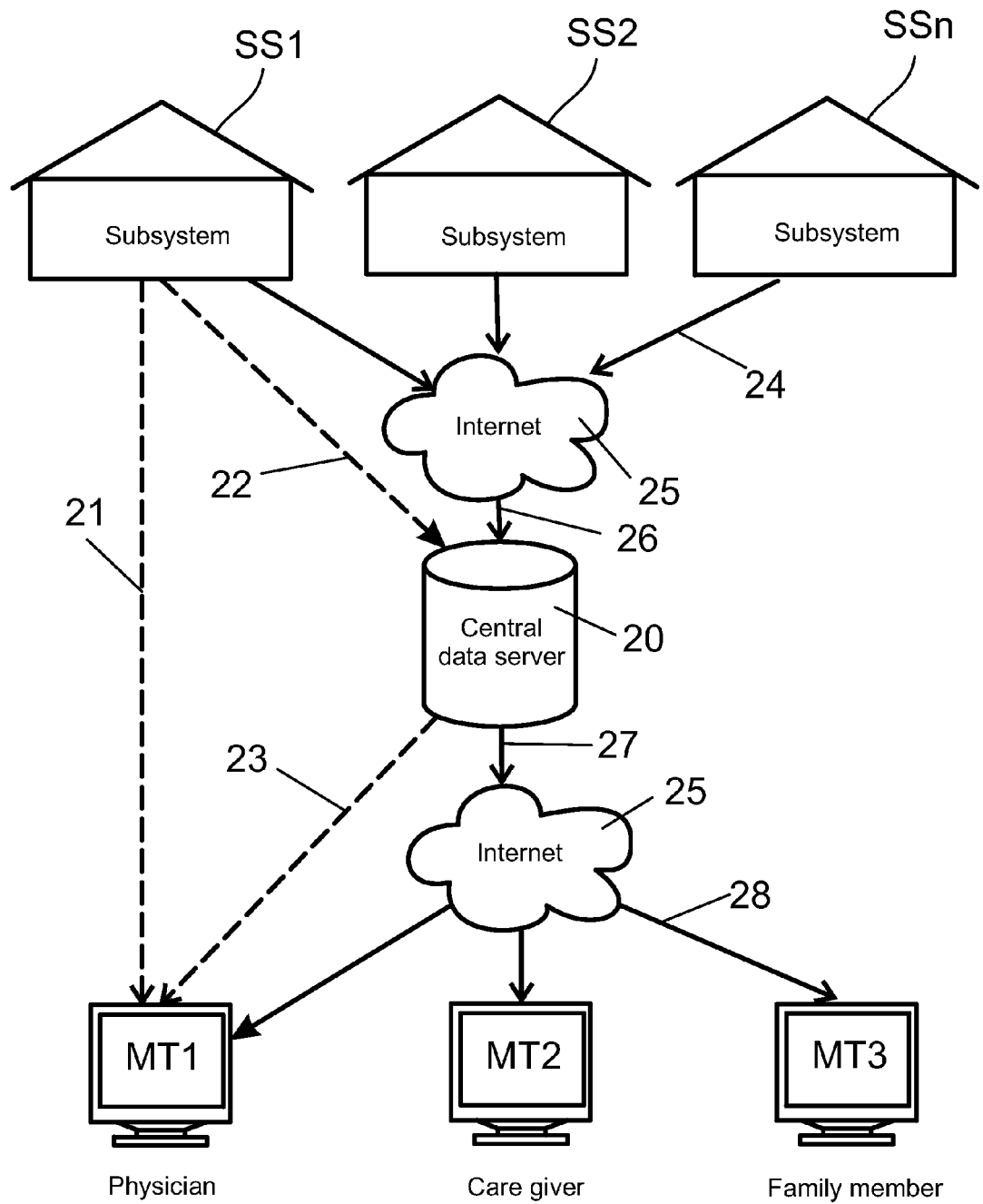
FIG. 1 is a schematic block diagram of a telecare or telehealth communication system for performing remote health monitoring according to an embodiment of the present invention.

Referring first to FIG. 1, a schematic block diagram of a telecare and/or telehealth communication system for performing remote health monitoring is schematically shown. The system comprises a plurality of remote health monitoring subsystems at the location of the individuals to be monitored distant from medical assistance, such as in a home environment. In an embodiment, a remote monitoring subsystem, such as subsystem SS1 may be connected to a monitoring terminal, such as monitoring terminal MT1 via a communication channel 21. The communication channel 21 may be either a radio or a cable communication channel. In this embodiment a monitoring person may have only access to one individual to be monitored at a time. Each change of the monitored person would require a reconnection to another communication channel. This problem can be solved by using a central communication and data server 20, which is capable of communicating with the remote monitoring subsystems SS1, SS2 and SS3 via data communication channels, through a cable or an air interface. In an embodiment, the system also comprises a number of monitoring terminals MT1, MT2 and MT3 which are capable of communicating with the central server station in order to provide information for the monitoring persons, such as health care professionals and/or care giving personnel and/or authorized family members. Each group of the monitoring persons has a predetermined access right category to access monitoring information provided by the remote monitoring subsystems and the central server unit 20. The health care professionals may for example be authorized to functionalities such as browsing patient data and setting up the monitoring parameters for the individual patient. The caregiver personnel may be authorized to browsing patient data and preparing different reports based on it. The family members may be authorized to have access to their respective relative in order to have information about his or her health condition. The monitoring terminals may be connected to the central server through either a radio communication channel or a cable communication channel, or a combination of a radio communication channel and a cable communication channel, such as the Internet. The use of the Internet as a communication channel makes it possible to set up the elements of the remote health monitoring system of according to embodiments of the present invention at any location of the world without any limitation. Therefore in a flexible configuration, the elements of the system, e.g. the remote monitoring subsystems SS1, SS2 and SS3 are connected through communication links 24, the central server unit 20 through communication links 26 and 27, and the monitoring terminals through communication links 28 to the Internet 25. In an embodiment as shown in the configuration of FIG. 1, the central server station receives and stores all the data from the connected subsystems and provides access to information about the health condition of all individuals included in the system to the authorized monitoring persons.

Figure 2:
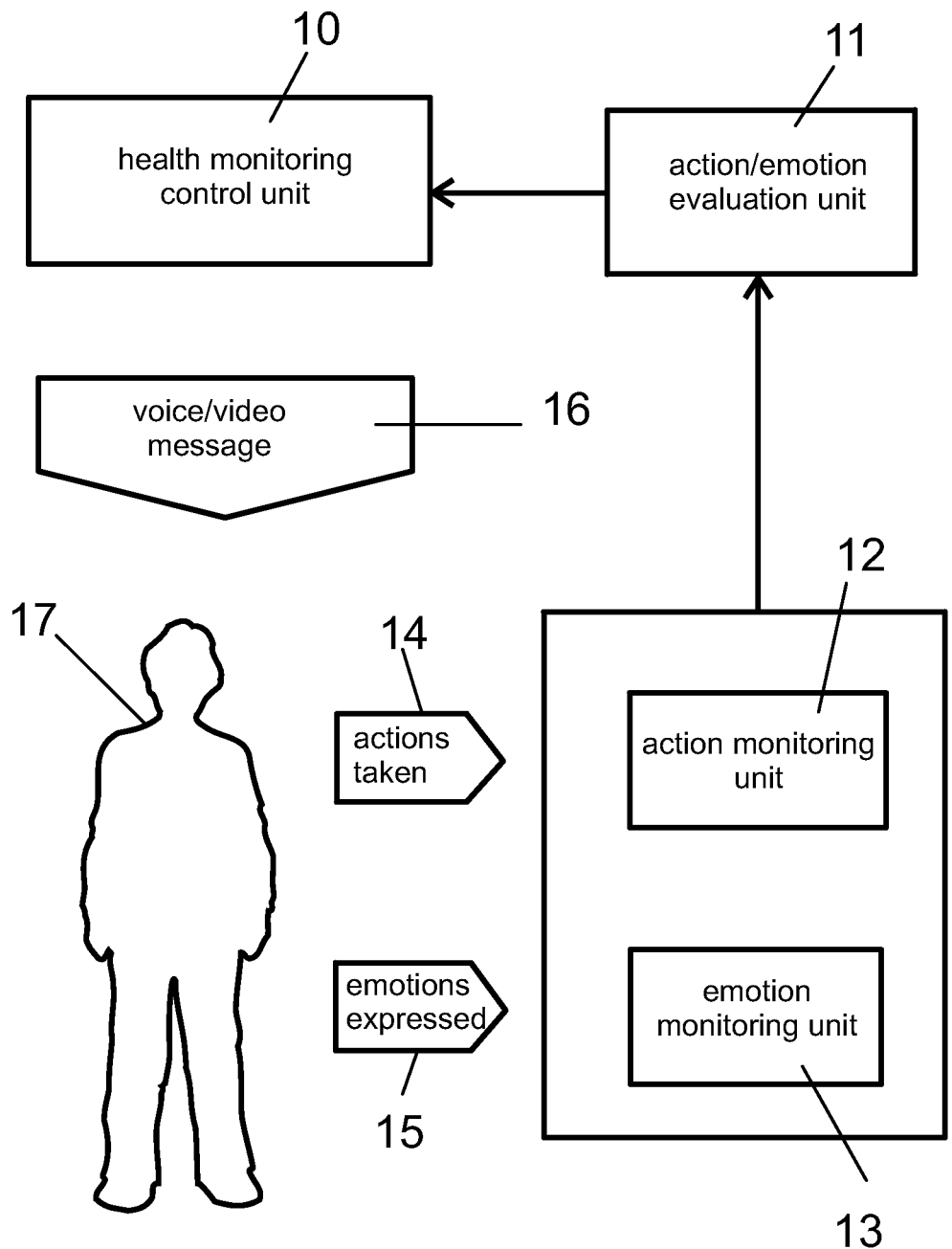
FIG. 2 is a schematic block diagram of the telecare or telehealth communication subsystem for performing the method according to an embodiment of the present invention.

The schematic block diagram of the telecare or telehealth communication subsystem for performing a method according to an embodiment of the present invention is shown in FIG. 2. The assisted person 17 receives voice messages which may be accompanied by corresponding video presentations, from the health monitoring control unit 10 which is the subsystem control unit (also called home hub). For this purpose, the health monitoring control unit 10 comprises a communication (voice and/or video message) storage for storing a series of predetermined voice messages for asking questions from or giving instructions to the assisted person 17, as it will be explained in more detail below. A program for determining an algorithm for communicating with the assisted person 17 is also stored in the health monitoring control unit 10. The messages for asking question or giving instructions are communicated to the assisted person 17 through an output means as indicated by reference sign 16. The remote health monitoring subsystem, as shown in FIG. 2, also comprises information collecting units 12, 13, 14, 15 with respect to the responsiveness and/or compliance characteristics of the assisted person 17 and means for analyzing and evaluating 11 the collected information. The actions 14 taken by the assisted person 17 are monitored by an action monitoring unit 12 and the emotions 15 expressed by this person 17 are monitored by an emotion monitoring unit 13. This information serves as a feedback to help determining or selecting the most effective form of communicating a message to the assisted person 17. The collected information may be stored in a storage located in the subsystem control unit or in a storage located in the central server station as well.

In addition to the description above, in an embodiment, the health monitoring control unit 10 is responsible for determining the timing of measurements, medication intake, and the announcement of various messages to be communicated with the assisted person 17. This message might be a reminder for a daily activity task e.g.: taking a walk outside or dealing with a virtual interactive pet or plant (which needs regular care). Such applications could also improve the communication frequency as well as the user's emotional connection to the home hub.

In order to increase the reliability of the telecare or telehealth communication system, the amount of the collected information may be increased, e.g. by collecting and storing of historical response information with respect to each assisted person 17 or collecting and storing of comparative response information from a plurality of assisted individuals.

Figure 3:
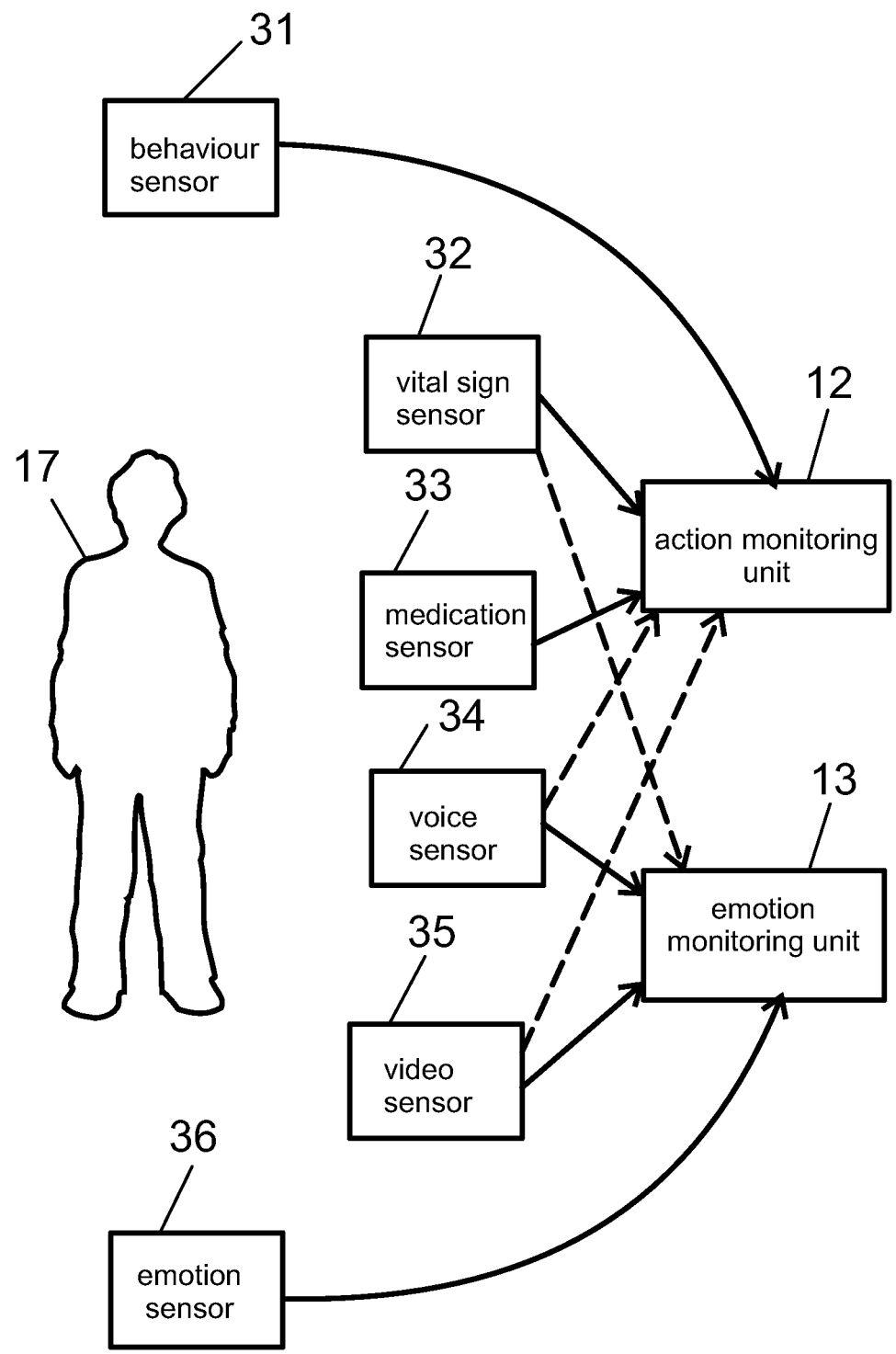
FIG. 3 is a schematic block diagram of the subsystem elements for performing the information collecting regarding compliance and/or responsiveness according to an embodiment of the present invention.

The collected information used as a feedback for evaluating the assisted person's responsiveness and/or compliance characteristics, may be based, for example but not limited to, on voice and video information relating to the assisted person's responsiveness and/or compliance, and/or vital sign and/or behavioral data relating to the assisted person's responsiveness and/or compliance and/or voice and video information relating to the assisted person's emotional status or response, as shown in FIG. 3. The information regarding to the responsiveness and/or compliance characteristics of the assisted individual is collected by an action monitoring unit 12 and an emotion monitoring unit 13. The action monitoring unit 12 may be connected to different sensors, which include, for example but not limited to: at least one behavior sensor 31, at least one vital sign sensor 32, at least one medication sensor 33, at least one voice sensor 34, and at least one video sensor 35. The emotion monitoring unit 13 may be connected to different sensors, which include, for example but not limited to: at least one vital sign sensor 32, at least one voice sensor 34, and at least one video sensor 35 and at least one emotion sensor 36. The dotted connecting lines and solid connecting lines of the vital sign sensor 32, voice sensor 34 and the video sensor 35 indicates that these sensors (or connections) may have two different functions, e.g. these sensors may be connected both to the action monitoring unit 12 and the emotion monitoring unit 13.

The health monitoring control unit 10 in FIG. 2. provides information about whether the monitored person 17 has performed the requested action or has taken the advice communicated to him or her.

A requested action is, for example, performing a measurement (e.g.: blood pressure measurement, blood glucose measurement, weight measurement, ECG measurement, etc.), taking medication, performing training, taking a walk outside, turning the heater to a higher temperature, turning off the air conditioner, or reducing the maximum water temperature in the house (elderly may have a decreased or changed sensation of cold, heat, pressure, vibration, touch and pain).

In an embodiment, the remote monitoring subsystem is connected with an adjustable heating system and air conditioning system, which has an appropriate interface to allow adjustment to be performed via electronic communication, some human performed actions would be unnecessary. However, since this may not be available in many houses, human intervention is necessary.

These data are stored in the action/emotion evaluator module's 11 in FIG. 2 or in a common database shared with the heath monitoring control unit 10, where the measurement data is stored as well.

A typical advice is to perform certain health measurements, to take the prescribed medications, or to perform certain tasks with the heath monitoring control unit's user interface.

The information collected by the health monitoring control unit 10 can relate to the elapsed time after requesting/advising an action needs to be performed by the monitored person 17, normal execution of the requested/advised action, failed execution of the requested/advised action, neglected execution of the requested/advised action, attempt to execute the same action multiple times, time between steps of execution, in case of not normal execution the activity that the person does instead of the requested/advised action, and tendency in the above-mentioned parameters aligned with the requested/advised action.

The software running on the health monitoring control unit 10 may be configured to include an algorithm to detect patterns of the emotional/action response's change over time. The emotional/action response's change may include a typical emotional response after setting up the system, or introducing a new measurement or new voice/video message in the patient's monitoring system. For example, introducing a new measurement will probably have a certain dynamics over time, where the user might be excited at the first time, but might be disappointed or bored later, or at the beginning the user might feel fear with the change of the device, but may gain acceptance over the time once the user is getting familiar with the change.

A study exploring people's personal and social emotional experience with health related portable interactive devices (Emotional Experience with Portable Health Devices, Rafael Gomez, Vesna Popovic, Alethea Blackler) found that negative experiences on a social level will be counter-productive to the overall experience perceived by the user.

To detect, and being able to identify these patterns plays a role in selecting the proper strategy of voice/video change. For example, in case the device is not well received at the first time use, that might not mean that the best strategy is to change the voice immediately, but the user might be facing a problem with learning how to handle the device.

The emotion monitoring unit 13 is able to detect the person's emotional status under everyday conditions. There are various methods the emotions are recognized from: facial expressions, voice or biometric data.

The emotion monitoring unit 13 may comprise a plurality of sensors that are able to perform measurements of physiological indicators, such as heart rate, skin conductivity, and skin temperature. The collected data are transmitted continuously from the sensors to the emotion monitoring unit 13 where each received data would get a time stamp. Data associated with the time stamps are stored in the remote monitoring subsystem's database as emotion events. This will allow the health monitoring control unit 10 to correlate them with other data.

Skin temperature and skin conductivity are sampled with a predefined sample rate. Heart rate may be measured in a various ways, where the data indicating a heart beat are sent by the heart rate sensor to the emotion monitoring unit 13 right after a heart beat has been detected. In order to interpret the signals from the emotion sensors the commonly used behavioral approach methods might be used, which may distinguish emotions in a two-part classification pairs like joy-anger, or happiness-sadness.

Figure 4:
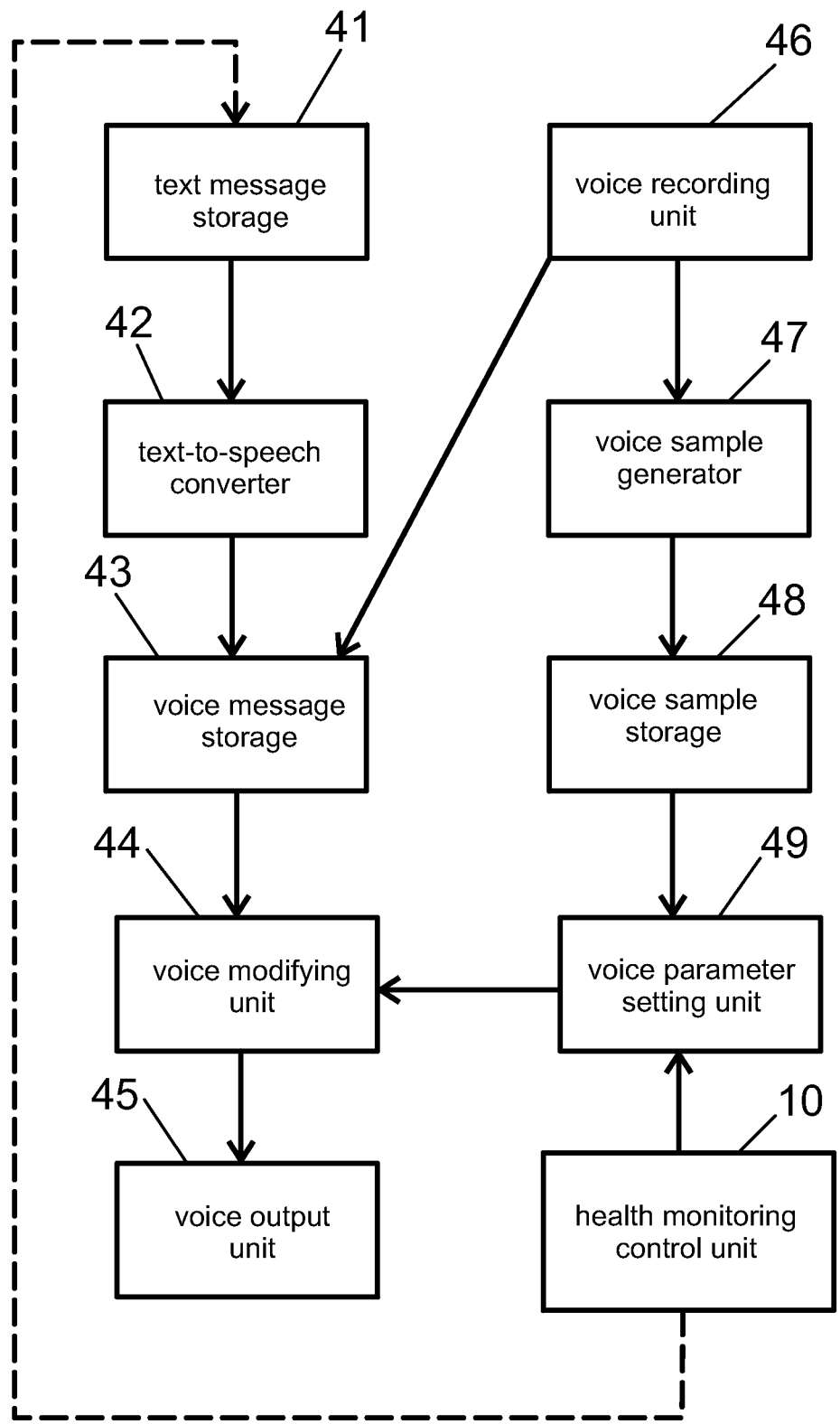
FIG. 4 is a schematic block diagram of the subsystem elements for generating the voice messages according to an embodiment of the present invention.

A schematic block diagram of the subsystem elements for generating the voice messages is shown in FIG. 4. In general, the voice messages may be generated based on text messages or pre-recorded voice messages. In case of using text messages, which may be stored in a text message storage 41, it will be necessary to convert these text messages in a text-to-speech converter 42. Such a text-to-speech converter is known, for example, from US Patent Publication No. 2005/0144002 A1. Text messages converted to voice messages may be stored in a voice message storage 43. In case of using pre-recorded voice messages, the voice messages may be pre-recorded in a voice recording unit 46 and then transferred to the voice message storage 43. Before the voice messages are communicated to the assisted person 17 through a voice output unit 45, the voice messages may be modified in a voice modification unit 44 in order to render the voice messages more acceptable and therefore more effective for the assisted person 17. This modification may be affected by modifying the voice setting parameters of the voice messages controlled by a voice parameter setting unit 49, which is connected to the health monitoring control unit 10. According to an embodiment, the voice parameter setting unit 49 may also be an integral part of the health monitoring control unit 10. The health monitoring control unit 10 carries out the control on the basis of the evaluation result received from the action/emotion evaluation unit 11 (shown in FIG. 2). The voice messages stored in the voice message storage 43 have substantially neutral character, e.g. no special emotional character. In order to make the voice messages more effective, the parameters of the voice message may be changed by adding non-verbal characteristics to the neutral voice messages. Such non-verbal characteristics are, for example but not limited to, the volume, pitch, intonation, accent, emphasis, emotional value, voice sample ID or any additional voice effect. Voice samples may be collected from any source or may be generated in a voice sample generator 47 which may receive input from the voice recording unit 46. The voice samples may be taken or generated from persons who are known to or respected by the assisted person 17. Voice messages using such voice samples might have the best effect on the assisted person 17. The voice output unit 45 or announcement device may be, for example, a loudspeaker. The loudspeaker may be placed at different fixed location in the home of the monitored person, or may be worn or carried by the monitored person, for example as a cell phone, which has the capability to make announcement with an appropriate voice level. For cost reduction purposes, the loud speaker can be mounted in the same housing as the health monitoring control unit 10 as well.

The set of predetermined text or voice messages, for example, might include the following samples: "please take your prescribed medications", "please measure your weight before you are having your breakfast", "please rest for 3 minutes before you perform your blood pressure measurement", "it is advised to increase your room temperature", etc.

Figure 5:
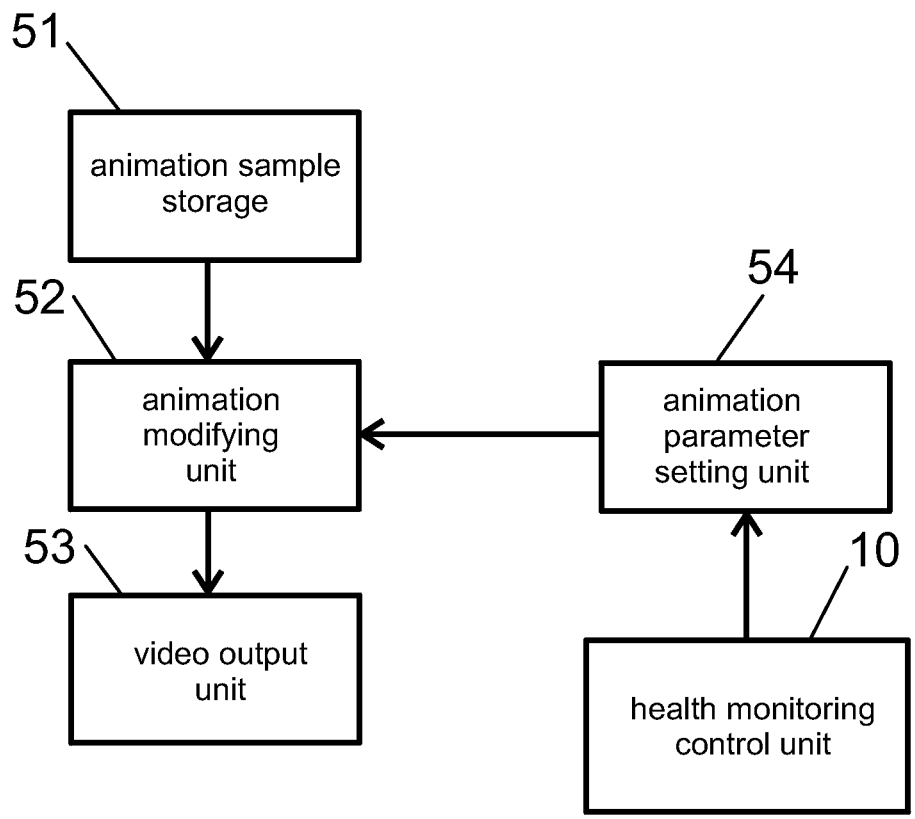
FIG. 5 is a schematic block diagram of the subsystem elements for generating the video messages on the basis of animation samples according to an embodiment of the present invention.

In order to further increase the efficiency of the communication between the system and the assisted person 17, the voice messages may also be accompanied by a video presentation resulting in a video message. The video presentation may be based on pre-recorded video samples or video animations. The subsystem elements for generating the video messages on the basis of animation samples are depicted in FIG. 5. In an embodiment, the animation samples are stored in an animation storage 51. The effect of the video message may also be increased by changing certain parameters of the video message. Such video setting parameters may include, for example but not limited to, gender and character of the performer, mimics, gestures (body language) or additional video effects. This modification may be affected by modifying the animation setting parameters of the video messages controlled by an animation parameter setting unit 54, which is connected to the health monitoring control unit 10. According to an embodiment, the animation parameter setting unit 54 may also be an integral part of the health monitoring control unit 10. The health monitoring control unit 10 carries out the control on the basis of the evaluation result received from the action/emotion evaluation unit 11 (shown in FIG. 2).

Figure 6:
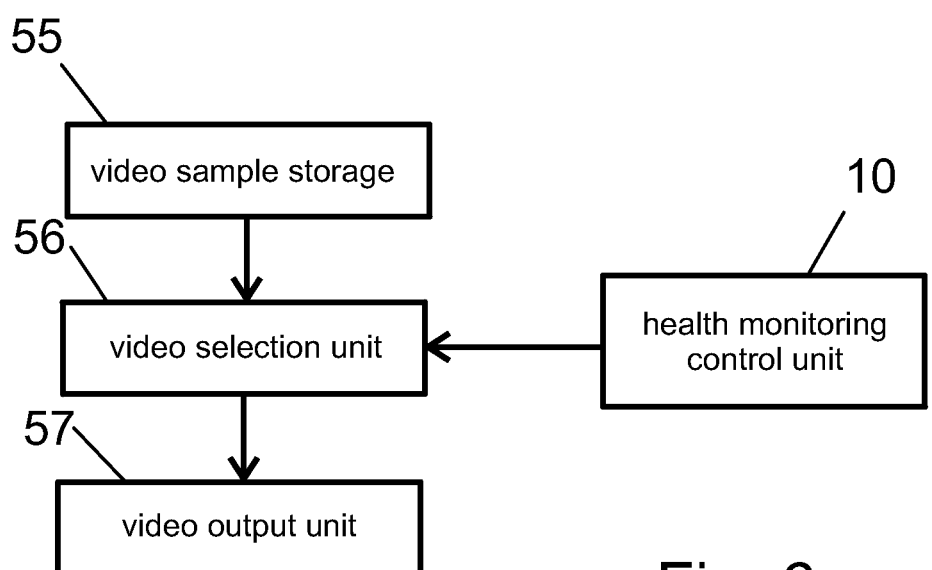
FIG. 6 is a schematic block diagram of the subsystem elements for generating the video messages on the basis of video samples according to an embodiment of the present invention.

The subsystem elements for generating the video messages on the basis of video samples are shown in FIG. 6. In an embodiment, the video samples are stored in a video sample storage 55 and the most effective video sample is selected in a video selection unit 56. The selected video presentation is communicated to the assisted person 17 by video output unit 57. The selection of the most effective video sample is controlled by the health monitoring control unit 10, which carries out the control on the basis of the evaluation result received from the action/emotion evaluation unit 11 (shown in FIG. 2).

Figure 7:
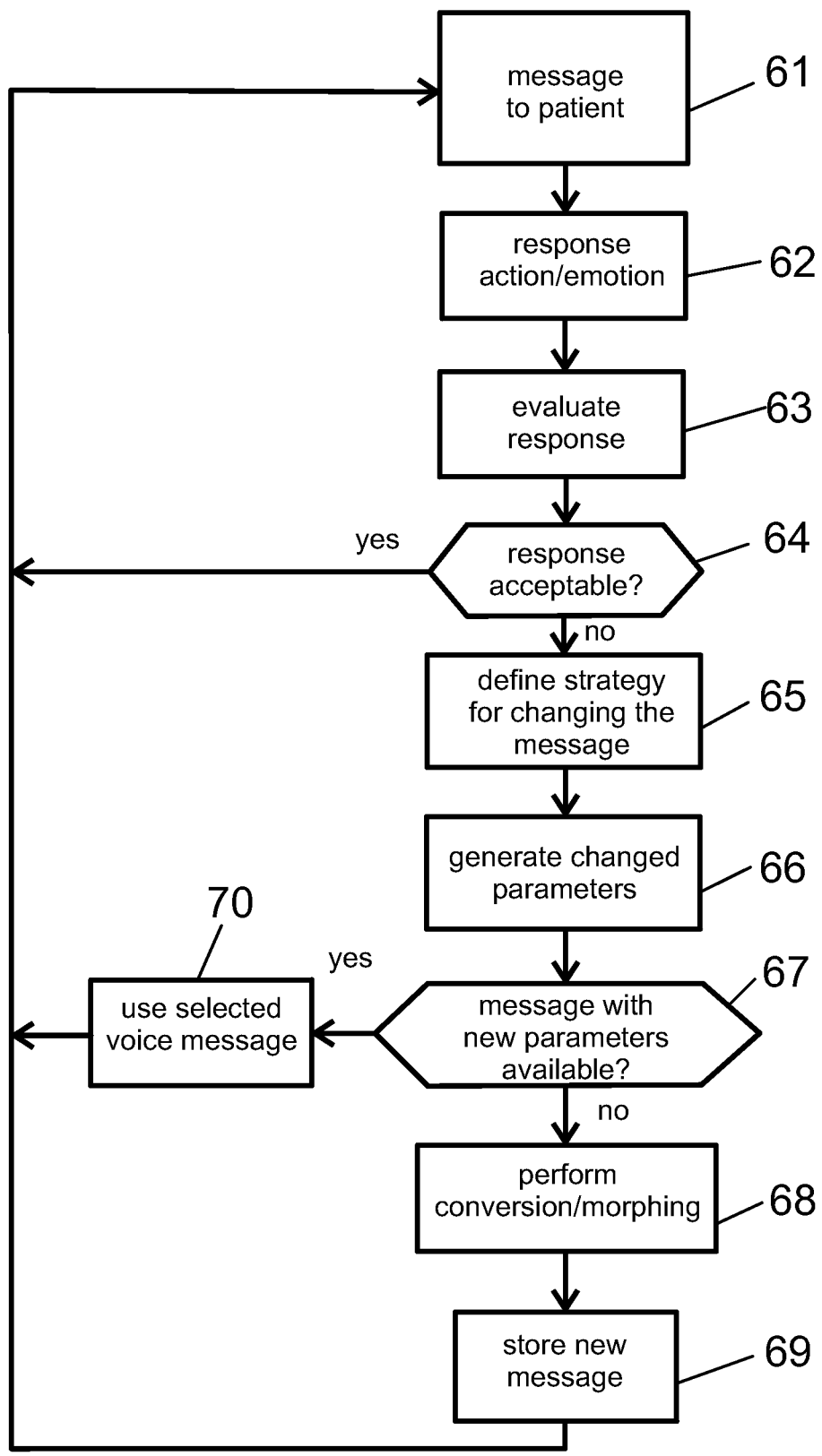
FIG. 7 is a schematic flow diagram of the method for providing more effective communication between the assisted persons and the monitoring system according to an embodiment of the present invention.

FIG. 7 is a schematic flow diagram of a method for providing more effective communication between the assisted person 17 and the monitoring system according to an embodiment of the present invention. The schedule and timing of messages for asking questions from or giving instructions to an assisted person are controlled by the health monitoring control unit 10. Each time when a voice or video message is communicated to the assisted person or patient 61, the response of the patient with regard to his/her action and/or emotion is detected 62 and evaluated 63. The response is examined to determine whether the response is acceptable or not 64. If the response is acceptable, the normal messaging algorithm is followed and, according to the programmed schedule and timing, a new message will be communicated to the patient 61 at a later time. However, if the response for any reason is not acceptable, a strategy will be determined in order to change the characteristics of the message 65. This strategy comprises simply repeating the message without any change at least once, or changing at least one of the parameter settings of the message. The new parameters for changing the message will be generated 66. The control unit examines whether a message with the determined new parameters already exist in the voice or video message storage (or database) 67. If yes, the message with the new parameters will be selected 70 and communicated to the patient 61. However, if the message with the new parameters cannot be found, the voice or video message with the new parameters will be generated 68 by a conversion or morphing method known per se. The newly generated voice or video message will be stored 69 for further use and the message with the new parameters will be communicated to the patient 61.

Another approach of determining the strategy for changing the characteristics of the message could involve the collecting and storing data relating to successful parameter selection. During evaluation, it can be examined how the emotional response of the patient changes in time in response to a communicated message. In this respect, the following cases may be of relevance. First, the monitored person's emotions do not change, or change in a positive way after the announcement. Second, the monitored person performs the desired actions, follows the given advices. Third, the monitored person performs the above-mentioned step within a reasonable time interval after the announcement.

If the algorithm in the action/emotion evaluation unit 11 detects any of the above mentioned cases, the strategy of selecting the utilized voice and/or video samples is considered to be successful. Thus the related parameters are stored in the database and marked with this information and may be transferred to the central data server. Storing these information from multiple patients allows the evaluation of strategies that are effective for a certain population.

In case the first or second response cannot be detected, a change of the voice or video message needs to be performed. If the change of the parameter settings is not sufficient, the system provides an option to change the text part of the message as well.

The parameter changing strategy for messages may include, for example but not limited to, the following: utilizing voice from the historical database that resulted in a better emotional response or the person had a quicker response with actions after the advices were given, utilizing other voice that is more efficient for the relevant population (in case this data is available in the central database—this data is collected on the central data server, and dynamically refreshed on data received from other monitored person's remote monitoring subsystem), and generating voice randomly, but within a limit of the desired voice characteristics, the limits are stored in the remote monitoring subsystem's database, furthermore, it can be changed from the central data server, which provides UI for the user to perform this task.

In an embodiment of the present invention, a telecare and/or telehealth communication method is provided, the method comprises providing predetermined voice messages for asking questions from or giving instructions to an assisted individual, providing an algorithm for communicating with the assisted individual, and communicating voice messages for asking questions from or giving instructions to the assisted individual on the basis of the predetermined voice messages. In an embodiment, the method further comprises analyzing the assisted person's responsiveness and/or compliance characteristics and providing the assisted person with the voice messages in a form most acceptable and effective for the individual on the basis of the analyzed responsiveness and/or compliance characteristics.

Taking into account of such an analysis of the assisted person's responsiveness and/or compliance characteristics will result in a communication more acceptable for the assisted person while rendering the method less expensive that the prior art human-to-human communication methods.

In order to increase the reliability of the method, the amount of the collected information may be increased, e.g. by collecting and storing of historical response information with respect to each assisted individual or collecting and storing of comparative response information from a plurality of assisted individuals.

The collected information used as a feedback for evaluating the assisted person's responsiveness and/or compliance characteristics, may be based, for example but not limited to, on voice and video information relating to the assisted person's responsiveness and/or compliance, and/or vital sign and/or behavioral data relating to the assisted person's responsiveness and/or compliance and/or voice and video information relating to the assisted person's emotional status or response.

The messages used in the method may be based on predetermined and stored text messages, which have to be converted to voice messages, or predetermined and recorded voice messages, with neutral character. In order to make these messages more effective, the parameters of the voice message may be changed in order to add non-verbal characteristics to the neutral voice messages. Such non-verbal characteristics are for example but not exclusively the volume, pitch, intonation, accent, emphasis, emotional value, voice sample ID or any additional voice effect. The voice samples may be taken or generated from persons who are known to (e.g. family member) or respected (e.g. famous doctor) by the assisted person. Voice messages using such voice samples might have the best effect on the assisted individual.

The voice messages may also be accompanied by a video presentation in order to provide a video message. The video presentation may be based on pre-recorded video samples or video animations. The effect of the video message may also be increased by changing certain parameters of the video message. Such video setting parameters may include, for example but not limited to, gender and character of the performer, mimics, gestures or additional video effects.

In an embodiment of the present invention, a telecare and/or telehealth communication system is proposed, which comprises a plurality of subsystems at the location of the individuals to be assisted, the subsystems comprising a subsystem control unit and at least one information collecting unit for collecting information from and relating to the assisted person, with at least a part of the information collecting units being capable of communicating with the subsystem control unit, a central data server station being capable of communicating with the subsystems, and monitoring side terminals being capable of communicating with the central station for providing information for health care professionals and/or care giving personnel and/or authorized family members, the subsystem control unit further comprising a communication storage for storing a series of predetermined voice messages for asking questions from or giving instructions to an assisted individual, a program for determining an algorithm for communicating with the assisted individual, and an output means for communicating the voice messages in order to ask questions from or to give instructions to an assisted individual.

The telecare and/or telehealth communication system further comprises means for analyzing and evaluating the information collected by the information collecting unit with respect to the responsiveness and/or compliance characteristics of the assisted person and means for providing the voice messages in a form most acceptable and effective for the individual on the basis of the analyzed responsiveness and/or compliance characteristics.

By using non-verbal communication signs bi-directionally in the user-machine communication, the effect of the communicated messages and therefore the compliance and/or responsiveness of the assisted persons may be increased sufficiently.

The elderly and chronically ill will be emotionally connected to the new systems and committed to that. The increased commitment, the more frequent usage and hence the improved medication and measurement compliance will be achieved.

On the one hand, the trusted voice of the loved one(s) or the respected person of the user would be used to remind the patient that there is time to perform some specific activities. This approach would help to overcome the impersonal technical barrier and would also help the user to not feel alone. On the other hand, the user in different state of mind, mood or physical situation may require different communication traits with adjusted text and adjusted non-verbal communication signs to become convinced by the telecare/telehealth system to do the certain task that helps maintaining and improving his/her health status.

Although embodiments of the present invention have been described on the basis of examples and with reference to the drawings, it may be appreciated by a person skilled in the art that the present invention is not limited to the shown and disclosed embodiments, but other elements, improvements and variations are also within the scope of the present invention.

What is claimed is:

1. A telecare and/or telehealth communication method comprising:
   providing, by a health monitoring control unit, predetermined voice messages configured to ask questions to or to give instructions to an assisted individual;
   providing an algorithm stored in the health monitoring control unit configured to communicate with the assisted individual;
   communicating, by the health monitoring control unit, at least one of the predetermined voice messages configured to ask questions to or to give instructions to the assisted individual;
   analyzing, by an evaluator unit, a responsiveness and/or compliance characteristics of the assisted individual, wherein the responsiveness and/or compliance characteristics comprise emotional response of the assisted individual; and
   providing, by the health monitoring control unit, the assisted individual with voice messages in a form most acceptable and effective for the assisted individual on the basis of the analyzed responsiveness and/or the analyzed compliance characteristics comprising the emotional response of the assisted individual.

2. The method of claim 1, wherein analyzing a responsiveness and/or compliance characteristics of the assisted individual comprises collecting and storing of historical response information with respect to each assisted individual.

3. The method of claim 1, wherein analyzing a responsiveness and/or compliance characteristics of the assisted individual comprises collecting and storing of comparative response information from a plurality of assisted individuals.

4. The method of claim 1, wherein analyzing a responsiveness and/or compliance characteristics of the assisted individual comprises collecting and storing voice and video information relating to the responsiveness and/or the compliance characteristics of the assisted individual.

5. The method of claim 1, wherein analyzing a responsiveness and/or compliance characteristics of the assisted individual comprises collecting and storing vital sign and/or behavioral data relating to the responsiveness and/or the compliance characteristics of the assisted individual.

6. The method of claim 1, wherein analyzing a responsiveness and/or compliance characteristics of the assisted individual comprises collecting and storing voice and video information relating to the emotional status or the emotional response of the assisted individual.

7. The method of claim 1, wherein the voice messages are stored in form of text messages which are convertible to voice messages with a neutral character.

8. The method of claim 1, wherein the voice messages are recorded and stored with a neutral character.

9. The method of claim 1, further comprising:
   providing a group of pre-recorded human voice samples; and
   selecting a human voice sample for modifying the voice messages.

10. The method of claim 9, wherein the human voice sample is selected from the group of pre-recorded human voice samples.

11. The method of claim 1, wherein in a case of non-compliance the at least one of the predetermined voice messages is repeated without changed voice setting parameters.

12. The method of claim 11, wherein the voice setting parameters comprise at least one of volume, pitch, intonation, accent, emphasis, emotional value, voice sample ID and additional voice effects.

13. The method of claim 1, wherein in a case of non-compliance the at least one of the predetermined voice messages is repeated with changed voice setting parameters.

14. The method of claim 1, wherein the voice messages are accompanied by a video presentation to form a video message.

15. The method of claim 14, wherein the video presentation is selected from a group of pre-recorded video samples or video samples in form of animations which might have effect on the assisted individual.

16. The method of claim 14, wherein in a case of non-compliance the video message is repeated with or without changed video setting parameters.

17. The method of claim 16, wherein the video setting parameters comprise gender and character of the performer, mimics, gestures and additional video effects.

18. The method of claim 17, wherein the video setting parameters are used in combination with the voice setting parameters.

19. A telecare and/or telehealth communication system comprising:
   a plurality of subsystems at the location of an assisted individual, wherein the plurality of subsystems comprises a subsystem control unit and at least one information collecting unit configured to collect information from and relating to the assisted individual, wherein at least one of the at least one information collecting unit is configured to communicate with the subsystem control unit;
   a central data server station configured to communicate with the plurality of subsystems; and
   monitoring side terminals configured to communicate with the central data server station and to provide information to health care professionals, care giving personnel, and/or authorized family members,
wherein the subsystem control unit comprises:
   a communication storage configured to store a series of predetermined voice messages configured to ask questions to or to give instructions to the assisted individual;

a program configured to determine an algorithm configured to communicate with the assisted individual;

an output communication configured to communicate voice messages in order to ask questions to or to give instructions to the assisted individual;

at least one information collecting unit;

a first processor configured to analyze and to evaluate information collected by the at least one information collecting unit with respect to a responsiveness and/or compliance characteristics of the assisted individual, wherein the responsiveness and/or compliance characteristics comprise emotional response of the assisted individual; and a second processor configured to determine the voice messages in a form most acceptable and effective for the assisted individual on the basis of the analyzed responsiveness and/or the analyzed compliance characteristics comprising the emotional response of the assisted individual.

20. The communication system of claim 19, further comprising an information collecting unit configured to collect and to store historical response information with respect to each assisted individual.

21. The communication system of claim 19, further comprising an information collecting unit configured to collect and to store comparative response information from a plurality of assisted individuals.

22. The communication system of claim 19, wherein the at least one information collecting unit comprises an information collecting unit configured to collect and to store voice and video information relating to the responsiveness and/or the compliance characteristics of the assisted individual.

23. The communication system of claim 19, wherein the at least one information collecting unit comprises an information collecting unit configured to collect and to store vital sign and/or behavioral data relating to the responsiveness and/or the compliance characteristics of the assisted individual.

24. The communication system of claim 19, wherein the at least one information collecting unit comprises an information collecting unit configured to collect and to store voice and video information relating to the emotional status or the emotional response of the assisted individual.

25. The communication system of claim 19, further comprising:
   a storage configured to store a series of predetermined text messages configured to ask questions to or to give instructions to the assisted individual; and
   a convertor configured to convert the text messages to appropriate voice messages in order to ask questions to or to give instructions to the assisted individual on the basis of the series of predetermined text messages.

26. The communication system of claim 19, wherein the communication storage is further configured to record and to store voice messages with a neutral character.

27. The communication system of claim 19, further comprising a storage configured to store at least one human voice sample.

28. The communication system of claim 27, wherein the communication storage is further configured to record and to store voice samples which have effect on the assisted individual.

29. The communication system of claim 19, wherein the subsystem control unit further comprises a voice parameter setting unit configured to change the characteristics of the voice messages.

30. The communication system of claim 29, wherein the voice parameter setting unit is configured to change at least one of the volume, pitch, intonation, accent, emphasis, emotional value, voice sample ID, and additional voice effects of the voice messages.

31. The communication system of claim 19, further comprising:
   a storage configured to store at least one video sample; and
   a third processor configured to select the video sample which has the best effect on the assisted individual;
   wherein the output communication is further configured to generate a video message as a combination of the video sample and a corresponding voice message.

32. The communication system of claim 31, further comprising a video parameter setting unit configured to change the characteristics of the video messages.

33. The communication system of claim 32, wherein the video parameter setting unit is further configured to change at least one of the gender and character of the performer, mimics, gestures and additional video effects of the video messages.

34. The method of claim 1, wherein the responsiveness and/or compliance characteristics of the assisted individual comprises action response of the assisted individual.

35. The method of claim 1, wherein analyzing a responsiveness and/or compliance characteristics of the assisted individual comprises collecting and storing voice and video information relating to the action response of the assisted individual.

36. The communication system of claim 19, wherein the responsiveness and/or compliance characteristics comprises action response of the assisted individual.

37. The communication system of claim 19, wherein the at least one information collecting unit comprises an information collecting unit configured to collect and to store voice and video information relating to the action response of the assisted individual.

* * * * *